United States Patent
Wang et al.

(10) Patent No.: US 9,044,205 B2
(45) Date of Patent: Jun. 2, 2015

(54) METHOD AND APPARATUS FOR OPTIMIZING MEDICAL DIAGNOSTIC TABLE OPERATION ACCORDING TO PATIENT'S WEIGHT

(75) Inventors: Feng Wang, Beijing (CN); Chengcheng Zhou, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 537 days.

(21) Appl. No.: 13/293,433

(22) Filed: Nov. 10, 2011

(65) Prior Publication Data

US 2012/0114107 A1    May 10, 2012

(30) Foreign Application Priority Data

Nov. 10, 2010    (CN) .......................... 2010 1 0552215

(51) Int. Cl.
*A61G 1/04* (2006.01)
*A61B 5/00* (2006.01)
*A61B 6/04* (2006.01)
*A61G 13/00* (2006.01)
*G01G 19/44* (2006.01)

(52) U.S. Cl.
CPC ............... *A61B 5/704* (2013.01); *A61B 6/0457* (2013.01); *A61G 13/0018* (2013.01); *A61G 2203/44* (2013.01); *G01G 19/445* (2013.01)

(58) Field of Classification Search
CPC ........ A61B 6/04; A61B 6/032; A61B 6/0421; A61B 6/0407
USPC ........ 378/208–209; 600/415, 427; 5/600–601
See application file for complete search history.

(56) References Cited

U.S. PATENT DOCUMENTS

| | | | |
|---|---|---|---|
| 6,381,780 | B1 | 5/2002 | Nose et al. |
| 7,050,532 | B2 | 5/2006 | Gohno |
| 7,706,498 | B2 | 4/2010 | Imai |
| 7,828,481 | B2 | 11/2010 | Ye et al. |
| 7,848,790 | B2 | 12/2010 | Pan et al. |
| 8,279,057 | B2 * | 10/2012 | Hirose ........................ 340/517 |
| 2011/0087416 | A1 * | 4/2011 | Patmore ........................ 701/93 |
| 2012/0117730 | A1 * | 5/2012 | Lemire et al. ..................... 5/611 |

* cited by examiner

*Primary Examiner* — Hoon Song
(74) *Attorney, Agent, or Firm* — Armstrong Teasdale LLP

(57) ABSTRACT

A method of optimizing operation of a medical diagnostic table according to a patient's weight is provided. The method includes sensing a weight carried by the medical diagnostic table using weighing sensors mounted under the medical diagnostic table, and adjusting a moving speed of the medical diagnostic table according to the sensed weight. The moving speed is reduced when the sensed weight is greater than a predetermined value, and the moving speed is increased when the sensed weight is less than the predetermined value.

20 Claims, 3 Drawing Sheets

METHOD AND APPARATUS FOR OPTIMIZING MEDICAL DIAGNOSTIC TABLE OPERATION ACCORDING TO PATIENT'S WEIGHT

CROSS REFERENCE TO RELATED APPLICATIONS

This application claims the benefit of Chinese Patent Application No. 201010552215.6 filed Nov. 10, 2010, which is hereby incorporated by reference in its entirety.

BACKGROUND OF THE INVENTION

The embodiments described herein relate to a medical instrument, in particular to a method and apparatus used in medical examination equipment for optimizing operation of a medical diagnostic table according to the patient's weight as well as a medical diagnostic table.

Operations of the existing medical examination equipment (e.g. a CT scanning and imaging machine), especially operations of the medical diagnostic table thereof, are closely related to the patient's weight in many aspects, or are limited by the patient's weight. However, the information of patient's weight is not involved in the system designs of the existing medical examination equipment.

Therefore, there is the need for a medical diagnostic table that can sense the patient's weight and can optimize its operation according to the sensed patient's weight.

SUMMARY OF THE INVENTION

The embodiments described herein provide a method and apparatus that can optimize operation of a medical diagnostic table according to the patient's weight as well as a medical diagnostic table so as to overcome the defects in the prior art.

According to the first aspect, a method of optimizing medical diagnostic table operation according to the patient's weight is provided. The method includes sensing the weight carried by the medical diagnostic table by means of the weighing sensors mounted under the medical diagnostic table; adjusting the moving speed of the medical diagnostic table according to the sensed weight, wherein when the sensed weight exceeds a predetermined value, the moving speed will be reduced; and when the sensed weight is under the predetermined value, the moving speed will be increased.

According to one embodiment, the method further includes moving the medical diagnostic table to a predetermined position without load when the sensed weight exceeds the predetermined limitation, and then proceeding to the next operation.

According to one embodiment, the method further includes moving the medical diagnostic table in a set high speed when no load is sensed.

According to one embodiment, the method further includes switching to table examination when a load is sensed.

According to one embodiment, the method further includes switching the medical diagnostic table to a standby mode when no load is sensed in a predetermined period of time.

According to one embodiment, the method further includes waking up the medical diagnostic table from the standby mode when a load is sensed.

According to one embodiment, the method further includes selecting a dose according to the sensed weight.

According to the second aspect, an apparatus of optimizing medical diagnostic table operation according to the patient's weight is provided. The apparatus includes a sensing module configured to sense the weight carried by the medical diagnostic table; an adjusting module configured to adjust the moving speed of the medical diagnostic table according to the sensed weight, wherein when the sensed weight exceeds a predetermined value, the moving speed will be reduced; and when the sensed weight is under the predetermined value, the moving speed will be increased.

According to one embodiment, the apparatus further includes a determining module configured to move the medical diagnostic table to a predetermined position without load when the sensed weight exceeds the predetermined limitation, and then proceed to the next operation.

According to one embodiment, the apparatus further includes a switching module configured to automatically switch to the table examination mode when the sensing module senses a load.

According to one embodiment, the switching module is configured to switch the medical diagnostic table to a standby mode when the sensing module senses no load in a predetermined period of time.

According to one embodiment, switching module is configured to wake up the medical diagnostic table from the standby mode when the sensing module senses a load.

According to one embodiment, apparatus further includes a selecting module configured to select a dose according to the sensed weight.

According to one embodiment, the medical diagnostic table is moved in a set high speed when the sensing module senses no load.

According to the third aspect, a medical diagnostic table for use in a medical examination equipment is provided. The table includes weighing sensors provided under the medical diagnostic table for weighing the load carried by the medical diagnostic table; an amplifier connected with the weighing sensors for amplifying signals from the weighing sensors; and an analog-to-digital converter connected with the amplifier for converting the amplified signals into digital signals and transmitting the digital signals to a controller.

According to one embodiment, the weighing sensors are provided between the table top and the base of the medical diagnostic table.

According to one embodiment, the weighing sensors are provided under the base of the medical diagnostic table.

According to the fourth aspect, a medical examination equipment is provided. The equipment includes the apparatus of optimizing medical diagnostic table operation according to the patient's weight according to the second aspect and/or the medical diagnostic table according to the third aspect.

The method and apparatus of optimizing medical diagnostic table operation according to the patient's weight as well as the medical diagnostic table can improve comfort of the subjects being examined during moving, examine over-weight subjects, optimize the work load, and select a dose according to the weight of the subject, meanwhile, the sensor and cables as well as other elements can be designed as a kit having customized configuration.

The present invention will be described in detail below by means of embodiments and in conjunction with the drawings, wherein the same or essentially the same components are denoted by the same reference numbers.

BEST MODES FOR CARRYING OUT THE INVENTION

Figure 1:
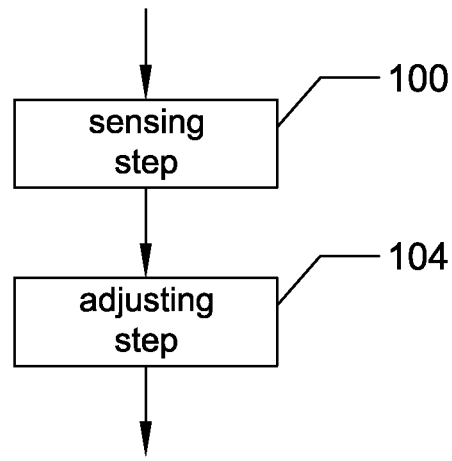
FIG. 1 is a flow chart of an exemplary method of optimizing operation of a medical diagnostic table according to the patient's weight.
Figure 2:
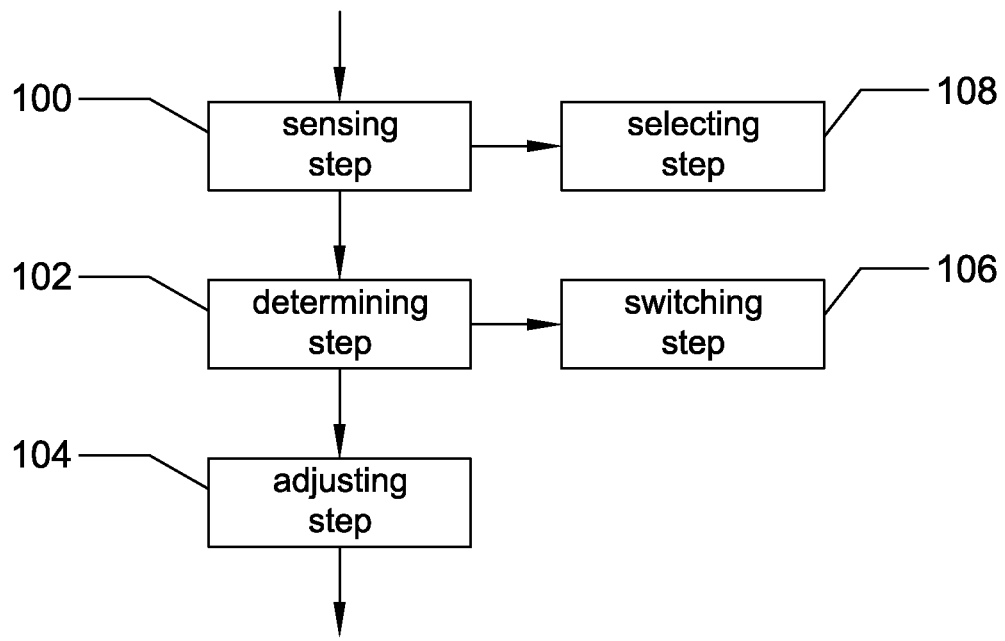
FIG. 2 is a flow chart of an exemplary method of optimizing operation of a medical diagnostic table according to the patient's weight.

FIG. 1 shows a flow chart of the method of optimizing operation of a medical diagnostic table according to the patient's. The method includes a sensing step 100 and an adjusting step 104. In other embodiments, the method may optionally include a determining step 102, a switching step 106 and/or a selecting step 108, as shown in FIG. 2.

In the sensing step 100, the weighing sensors provided under the medical diagnostic table are used to sense the weight carried by the medical diagnostic table.

In the adjusting step 104, the moving speed of the medical diagnostic table is adjusted according to the sensed weight. For example, the moving speed of the medical diagnostic table is adjusted by using the control system of the medical examination equipment to adjust the speed of the motor driving the medical diagnostic table. When the sensed weight exceeds a predetermined value, the moving speed is reduced. When the sensed weight is under the predetermined value, the moving speed is increased. Specifically, clinical researches and analyses show that for a subject being examined with a normal weight (e.g. about 75 kg), the normal moving speed of the medical diagnostic table is 37.5 m/s, which makes the subject feel comfortable. However, for a relatively heavy subject being examined (e.g. about 150 kg), the normal speed makes the subject feel uncomfortable, so the moving speed of the medical diagnostic table needs to be reduced. It has been proven by experiments that the moving speed of the medical diagnostic table can be adjusted according to the relationship that the weight is inversely proportional to the speed. For example, for a subject being examined having a weight of about 150 kg, a comfortable moving speed is about 18 m/s.

In one embodiment, when no load is sensed, the medical diagnostic table is made to move in a set high speed, for example, twice the normal speed, by means of the control system so as to reduce the time of operation.

In one embodiment, the determining step 102 is used to determine whether the sensed weight exceeds the predetermined limitation. Specifically, an ordinary medical diagnostic table has a load limitation of 220 kg during moving. This load limitation keeps subjects heavier than 220 kg away from examination. However, when the medical diagnostic table is in a stop mode, with the motor brakes engaged, it can support a load up to 300-350 kg without any safety problem. Thus if it is determined in the determining step that the sensed weight exceeds the predetermined limitation, the medical diagnostic table is made to move to the predetermined position without load first and then the subject being examined gets on the medical diagnostic table to proceed with the next operation.

In one embodiment, the method of optimizing operation of a medical diagnostic table according to the patient's weight further includes a switching step 106, wherein the medical diagnostic table is switched to an examination mode by the control system when a load is sensed on the medical diagnostic table. In another embodiment, the switching step 106 is used to switch the medical diagnostic table to a standby mode when no load is sensed on the medical diagnostic table in a predetermined period of time (e.g. about 5-10 minutes). In another embodiment, the switching step 106 is used to wake up the medical diagnostic table when a load is sensed on the medical diagnostic table.

In one embodiment, the method of optimizing operation of a medical diagnostic table according to the patient's weight may further include a selecting step 108, wherein the dose, e.g. the dose for X-ray irradiation, is selected according to the sensed weight.

Figure 3:
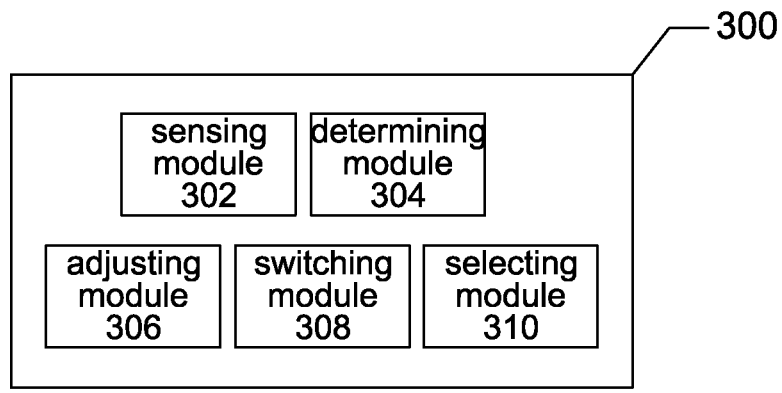
FIG. 3 is a schematic diagram of the apparatus of optimizing operation of a medical diagnostic table according to the patient's weight according to one embodiment.

FIG. 3 is a schematic diagram of the apparatus 300 of optimizing operation of a medical diagnostic table according to the patient's weight according to one embodiment. The apparatus 300 includes a sensing module 302 and an adjusting module 306. In other embodiments, the apparatus may optionally include a determining module 304, a switching module 308, and/or a selecting module 310. These modules can be implemented as software, hardware, firmware or a combination thereof The sensing module 302 is used to perform step 100, the determining module 304 is used to perform step 102, the adjusting module 306 is used to perform step 104, the switching module 308 is used to perform step 106, and the selecting module 310 is used to perform step 108.

Figure 4:
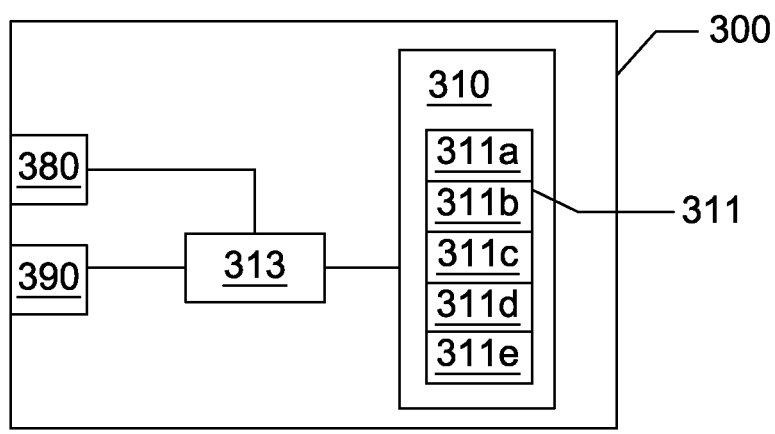
FIG. 4 is a schematic diagram of the apparatus of optimizing operation of a medical diagnostic table according to the patient's weight according to another embodiment.

FIG. 4 is another embodiment of the apparatus 300 of optimizing operation of a medical diagnostic table according to the patient's weight. The apparatus 300 includes a processing unit 313, such as MCU, DSP or CPU etc. The processing unit 313 may be a single unit or multiple units to perform the different steps. In addition, the apparatus 300 may optionally include an interactive interface 380 and an output unit 390. Moreover, the apparatus 300 further includes at least one computer program product 310 in the form of a non-volatile memory, such as EEPROM, flash memory or hard-disc drive or the like. The computer program product 310 includes a computer program 311 having program codes. When running, the program codes cause the apparatus 300 to perform the steps as shown in FIG. 1 or 2.

Specifically, the program codes in the computer program 311 of the apparatus 300 include a sensing module 311a for performing step 100; a determining module 311b for performing step 102; an adjusting module 311c for performing step 104; a switching module 311d for performing step 106; and a selecting module 311e for performing step 108. In other words, when different modules 311a-311e are run on the processing unit 313, they correspond to modules 302, 304, 306, 308 and 310 as shown in FIG. 3.

Figure 5:
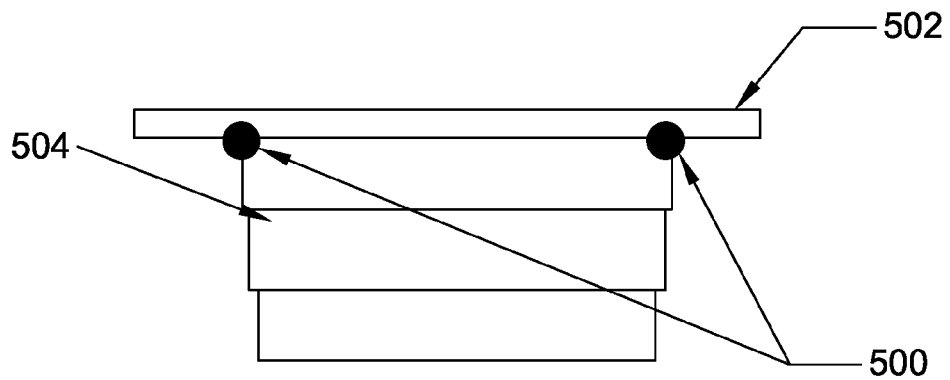
FIG. 5 is a schematic diagram of the medical diagnostic table for use in a medical examination equipment according to one embodiment.
Figure 6:
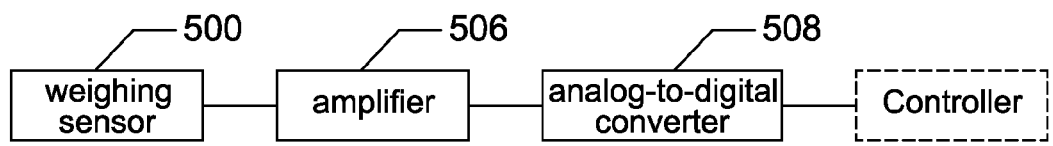
FIG. 6 is a block diagram of the circuit of the medical diagnostic table according to one embodiment.

FIG. 5 is a schematic diagram of the medical diagnostic table for use in a medical examination equipment according to one embodiment. The medical diagnostic table includes weighing sensors 500, which are provided between the table top 502 and the base 504 of the medical diagnostic table. FIG. 6 is a block diagram of the circuit of the medical diagnostic table according to one embodiment. The circuit includes an amplifier 506 connected with the weighing sensors 500 as well as an analog-to-digital converter 508.

The weighing sensors 500 may be the appropriate number (e.g. four) of tecsis or Honeywell sensors which are provided under the medical diagnostic table for sensing the weight of the load on the medical diagnostic table.

The output signals of the sensors 500 are usually in a level of millivolt, thus an amplifier 506 connected with the weighing sensors 500 is needed for amplifying signals from the weighing sensors. The analog-to-digital converter 508 is connected with the amplifier 506 for converting the amplified signals into digital signals and for transmitting the digital signals to the controller of the medical examination equipment. In view of distortion of the analog signals during transmission in the cables, thus, the analog-to-digital converter 508 may be placed as close as possible to the weighing sensors.

Figure 7:
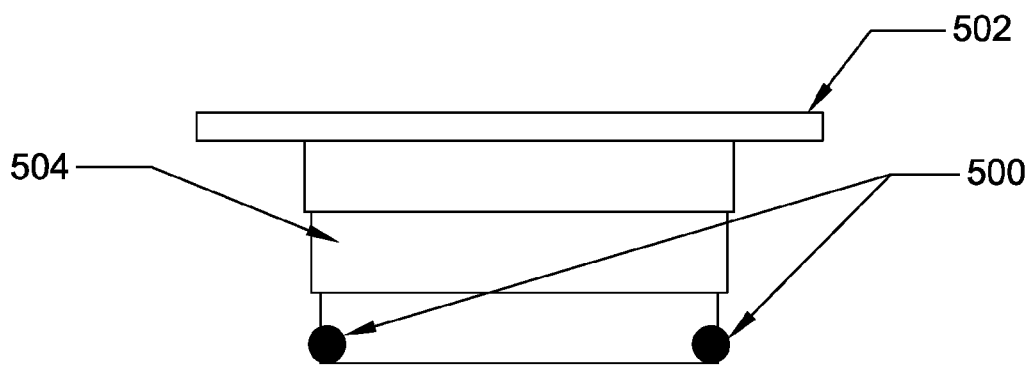
FIG. 7 is a schematic diagram of the medical diagnostic table for use in a medical examination equipment according to another embodiment.

In another embodiment, the weighing sensors 500 are provided under the base 504 of the medical diagnostic table, as shown in FIG. 7, in this way little change is made to the structure of the existing medical diagnostic table.

When using four sensors in the medical diagnostic table of the above embodiment for sensing, a satisfactory precision of sensing may be obtained. Load tests ranging from 0 to 300 kg show that the maximum error is less than 0.3 kg, which is less than 0.1%. The test results are as shown in Tables 1 and 2 below, wherein Table 1 shows the test results of a normal load (i.e. the load being at the middle of the medical diagnostic table) and Table 2 shows the test results of an offset load (i.e. the load being at one side of the medical diagnostic table) so as to cover the imbalanced condition that may occur in actual application.

TABLE 1

Test results of normal load

| | | | Weight (kg) | | | |
|---|---|---|---|---|---|---|
| 0 | 50 | 100 | 150 | 200 | 250 | 300 |

| Test result (kg) | 0.04 | 49.97 | 100.03 | 150.03 | 200.08 | 250.14 | 300.06 |

TABLE 2

Test results of offset load

| | | | Weight (kg) | | | |
|---|---|---|---|---|---|---|
| 0 | 10 | 40 | 70 | 100 | 130 | 160 |

| Test result (kg) | 0.04 | 9.92 | 39.96 | 69.95 | 99.80 | 129.90 | 159.91 |

The apparatus of optimizing operation of a medical diagnostic table according to the patient's weight and/or the medical diagnostic table according to the above embodiments can be implemented in such medical examination equipment including various X-ray machines, MRs, ultrasonic detection devices and CT scanning and imaging devices and the like through software, hardware, firmware or a combination thereof. Such implementation is easy for those skilled in the art, so it will not be detailed herein.

While the present invention has been described in conjunction with specific embodiments, the present invention is not limited to said specific embodiments. Those skilled in the art shall understand that various modifications, equivalent substitutions and variations and the like can be made to the invention, for example, one step or module in said embodiments can be divided into two or more steps or modules, or on the contrary, the functions of two or more steps or modules in said embodiments can be realized in one step or module. Therefore, such variations should fall within the protection scope of the present invention as long as they are not departing from the spirit of the present invention. In addition, some terms used in the description and claims of this application are not intended to limit but only to facilitate descriptions. Furthermore, expressions like "one embodiment" and "another embodiment" used in this text mean different embodiments, but of course, they can be combined fully or in part into one embodiment.

The invention claimed is:

1. A method of optimizing operation of a medical diagnostic table according to a patient's weight, said method comprising:
    sensing a weight carried by the medical diagnostic table using weighing sensors mounted under the medical diagnostic table; and
    adjusting a moving speed of the medical diagnostic table according to the sensed weight, wherein the moving speed is reduced when the sensed weight is greater than a predetermined value, and the moving speed is increased when the sensed weight is less than the predetermined value.

2. The method according to claim 1, further comprising moving the medical diagnostic table to a predetermined position without a load when the sensed weight is greater than a predetermined limitation, and proceeding to a next operation.

3. The method according to claim 1, further comprising moving the medical diagnostic table at a set high speed when no load is sensed.

4. The method according to claim 1, further comprising switching to a table examination mode when a load is sensed.

5. The method according to claim 1, further comprising switching the medical diagnostic table to a standby mode when no load is sensed during a predetermined period of time.

6. The method according to claim 5, further comprising Lemireng up the medical diagnostic table from the standby mode when a load is sensed.

7. The method according to claim 1, further comprising selecting a dose according to the sensed weight.

8. An apparatus for optimizing operation of a medical diagnostic table according to a patient's weight, said apparatus comprising:
    a sensing module configured to sense a weight carried by the medical diagnostic table; and
    an adjusting module configured to adjust a moving speed of the medical diagnostic table according to the sensed weight, wherein the moving speed is reduced when the sensed weight is greater than a predetermined value, and the moving speed is increased when the sensed weight is less than the predetermined value.

9. The apparatus according to claim 8, further comprising a determining module configured to move the medical diagnostic table to a predetermined position without a load when the sensed weight is greater than a predetermined limitation, and to proceed to a next operation.

10. The apparatus according to claim 8, further comprising a switching module configured to automatically switch to a table examination mode when the sensing module senses a load.

11. The apparatus according to claim 10, wherein said switching module is configured to switch the medical diagnostic table to a standby mode when the sensing module senses no load during a predetermined period of time.

12. The apparatus according to claim 10, wherein said switching module is configured to wake up the medical diagnostic table from a standby mode when the sensing module senses a load.

13. The apparatus according to claim 8, further comprising a selecting mode configured to select a dose according to the sensed weight.

14. The apparatus according to claim 8, wherein the medical diagnostic table is configured to be moved at a set high speed when the sensing module senses no load.

15. A medical diagnostic table for use in a medical examination equipment, said table comprising:
   weighing sensors under a medical diagnostic table and configured to weigh a load carried by the medical diagnostic table;
   an amplifier connected to the weighing sensors and configured to amplify signals from the weighing sensors;
   an analog-to-digital converter connected to the amplifier and configured to covert the amplified signals into digital signals and to transmit the digital signals; and
   a controller configured to receive the digital signals from the analog-to-digital converter and adjust a moving speed of the medical diagnostic table according to the sensed weight, wherein the moving speed is reduced when the sensed weight is greater than a predetermined value, and the moving speed is increased when the sensed weight is less than the predetermined value.

16. The medical diagnostic table according to claim 15, wherein the weighing sensors are provided between a table top and a base of the medical diagnostic table.

17. The medical diagnostic table according to claim 15, wherein the weighing sensors are provided under a base of the medical diagnostic table.

18. The apparatus according to claim 8, wherein the sensing module comprises weighing sensors between a table top and a base of the medical diagnostic table.

19. The apparatus according to claim 8, wherein the sensing module comprises weighing sensors under a base of the medical diagnostic table.

20. The apparatus according to claim 8, wherein the sensing module comprises:
   weighing sensors under a medical diagnostic table and configured to weigh a load carried by the medical diagnostic table;
   an amplifier connected to the weighing sensors and configured to amplify signals from the weighing sensors; and
   an analog-to-digital converter connected to the amplifier and configured to covert the amplified signals into digital signals and to transmit the digital signals to a controller of the medical examination equipment.

* * * * *